US008741278B2

(12) United States Patent
Carlson et al.

(10) Patent No.: US 8,741,278 B2
(45) Date of Patent: Jun. 3, 2014

(54) COMPOSITION AND METHOD FOR REDUCING BLOOD GLUCOSE LEVELS

(76) Inventors: Kameron Jay Carlson, Sioux Falls, SD (US); Nancy Ann Carlson, Sioux Falls, SD (US)

( * ) Notice: Subject to any disclaimer, the term of this patent is extended or adjusted under 35 U.S.C. 154(b) by 367 days.

(21) Appl. No.: 12/869,396

(22) Filed: Aug. 26, 2010

(65) Prior Publication Data

US 2011/0212216 A1    Sep. 1, 2011

Related U.S. Application Data

(60) Provisional application No. 61/275,151, filed on Aug. 26, 2009, provisional application No. 61/275,541, filed on Aug. 31, 2009.

(51) Int. Cl.
*A01N 63/00* (2006.01)
*A01N 63/04* (2006.01)

(52) U.S. Cl.
USPC ...................................... 424/93.1; 424/93.51

(58) Field of Classification Search
USPC ............................................. 424/93.1, 93.51
See application file for complete search history.

(56) References Cited

U.S. PATENT DOCUMENTS

| | | |
|---|---|---|
| 5,087,623 A | 2/1992 | Boynton et al. |
| 5,545,410 A | 8/1996 | Fox et al. |
| 5,612,074 A | 3/1997 | Leach |
| 5,614,224 A | 3/1997 | Womack |
| 6,365,176 B1 | 4/2002 | Bell et al. |
| 6,689,385 B2 | 2/2004 | Richardson et al. |
| 2001/0002269 A1 | 5/2001 | Zhao |
| 2002/0015761 A1 | 2/2002 | Prosise et al. |
| 2003/0087019 A1 | 5/2003 | Malkki et al. |
| 2006/0078533 A1 | 4/2006 | Omoigui |
| 2007/0212470 A1 | 9/2007 | Cherukuri et al. |
| 2008/0032005 A1 | 2/2008 | Fu et al. |
| 2008/0193590 A1 | 8/2008 | Lundberg |
| 2008/0254168 A1 | 10/2008 | Mueller et al. |
| 2009/0011078 A1 | 1/2009 | Johnson |
| 2009/0208612 A1 | 8/2009 | Reiser et al. |
| 2010/0166918 A1* | 7/2010 | Miller ............................ 426/73 |

FOREIGN PATENT DOCUMENTS

JP    2002-326951    11/2002

OTHER PUBLICATIONS

Nature's Bounty Diabetic Support Pack (http://www.walgreens.com/store/c/nature's-bounty-diabetic-support-pack--30day-supply/ID=prod3430763-product. On sale on or before Mar. 14, 2008).*
"Is Wheat Germ Good for You?" (http://vegetarian.lovetoknow.com/Is_Wheat_Germ_Good_for_You 2006-2012).*
Katz et al. (As Scientific Review of the Health Benefits of Oats. 2001. The Quaker Oats Company, pp. 1-11).*
Art of Record: "Brewer's Yeast". University of Maryland. 2011. pp. 1-6.*
Mani et al. (Effect of Wheat Bran Supplementation on blood sugar, glycosylated protein and serum lipids in NIDDM subjects. Plant Foods for Human Nutrition (1987) 37: 161-168).ion 37:161-168 (1987.*
Dia-Treaties by Vintek Nutrition (www.flickr.com/photos/vinyrknutrtion/6283078571. May 15, 2005).*
American Diabetes Association (http://www.diabetes.org/living-with-diabetes/treatment-and-care/medication/insulin/insulin-routines.html).*
Hlebowicz, J. et al., "Effect of cinnamon on postprandial blood glucose, gastric emptying, and satiety in healthy subjects," *Am. J. Clin. Nutr.*, vol. 85, pp. 1552-1556 (2007).
Hlebowicz, J. et al., "Effect of commercial breakfast fibre cereals compared with corn flakes on postprandial blood glucose, gastric emptying and satiety in healthy subjects: a randomized blinded crossover trial," *Nutrition Journal*, vol. 6, No. 22, pp. 1-7 (2007).
International Search Report and Written Opinion mailed Dec. 13, 2010.
Racek, J. et al., "Influence of Chromium-Enriched Yeast on Blood Glucose and Insulin Variables, Blood Lipids, and Markers of Oxidative Stress in Subjects with Type 2 Diabetes Mellitus," *Biological Trace Element Research*, vol. 109, pp. 215-230 (2006).
Anderson et al., "Metabolic Effects of Insoluble Oat Fiber on Lean men with Type II Diabetes," *American Association of Cereal Chemists, Inc.*, vol. 68, No. 3, 1991.
Anderson, "Chromium, Glucose Intolerance and Diabetes," *Journal of the American College of Nutrition*, vol. 17, No. 6, 548-555 (1998).
Blevins et al., "Effect of Cinnamon on Glucose and Lipid Levels in Non-Insulin-Dependent Type 2 Diabetes," *Diabetes Care*, vol. 30, No. 9, Sep. 2007.
Cefalu, "Intensive Diabetes Control: Reaping the Benefits Promised by Clinical Trials," www.cadre-diabetes.org, Dec. 2004.
Chandalia et al., "Beneficial Effects of High Dietary Fiber Intake in Patients with Type 2 Diabetes Mellitus," *The New England Journal of Medicine*, May 11, 2000.
DeMunter et al., "Whole Grain, Bran, and Germ Intake and Risk of Type 2 Diabetes: A Prospective Cohort Study and Systematic Review," *PLoS Medicine*, Aug. 2007, vol. 4, Issue 8.
"Insulin Resistance and Pre-diabetes," U.S. Department of Health and Human Services, National Institutes of Health, NIH Publication No. 09-4893, Oct. 2008.
Khan et al., "Cinnamon Improves Glucose and Lipids of People with Type 2 Diabetes," *Diabetes Care*, vol. 26, No. 12, Dec. 2003.
Langer, "Chromium picolinate: the biochemical wonder," *Better Nutrition*, 1989-90, Feb. 1990.
Maryniuk, "Patent Education: Addressing Multiple Risk Factors Through Medical Nutrition Therapy," www.cadre-diabetes.org, Dec. 2004.

(Continued)

*Primary Examiner* — Karen Cochrane Carlson
*Assistant Examiner* — Natalie Moss
(74) *Attorney, Agent, or Firm* — Merchant & Gould P.C.

(57) ABSTRACT

The present invention relates to a composition and method for reducing blood glucose levels in a mammal, such as canines and humans. The composition includes bran, cinnamon, yeast, gelatin, and optionally, wheat germ oil, octacosanol, and/or flavor. The method includes administering the composition to the mammal and, if the composition lacks wheat germ oil, also administering wheat germ oil to the mammal.

13 Claims, 10 Drawing Sheets

(56) References Cited

OTHER PUBLICATIONS

McDuffie, "Overcoming Barriers to Intensive Insulin Administration," www.cadre-diabetes.org, Dec. 2004.

Meletis, et al., "Natural Approaches to the Prevention and Management of Diabetes Mellitus," *Alternative & Complementary Therapies*, Jun. 2001.

Nahas et al., "Complementary and Alternative Medicine for the Treatment of Type 2 Diabetes," *Canadian Family Physician*, vol. 55, Jun. 2009.

Offenbacher et al., "Beneficial effect of chromium-rich yeast on glucose tolerance and blood lipids in elderly subjects," *Diabetes*, Nov. 1980, vol. 29, No. 11, 919-925.

Preuss et al., "Whole Cinnamon and Aqueous Extracts Ameliorate Sucrose-Induced Blood Pressure Elevations in Spontaneously Hypertensive Rats," *Journal of the American College of Nutrition*, vol. 25, No. 2, 144-150 (2006).

Venn et al., "Cereal grains, legumes and diabetes," *European Journal of Clinical Nutrition*, (2004) 58, 1443-1461.

Vetsulin® product information, 2006.

Zimmerman, "The Truth About Sugar," *Nutrition*, Dec. 2009.

Miscellaneous Information from Internet, Sep. 2010.

\* cited by examiner

COMPOSITION AND METHOD FOR REDUCING BLOOD GLUCOSE LEVELS

CROSS-REFERENCE TO RELATED APPLICATIONS

This application claims benefit of Provisional Application No. 61/275,151, filed Aug. 26, 2009 and Provisional Application No. 61/275,541, filed Aug. 31, 2009, which applications are incorporated herein by reference.

FIELD OF THE INVENTION

The present invention relates to a composition and method for reducing blood glucose levels in a mammal, such as a canine or human. The composition includes bran, cinnamon, yeast, gelatin, and optionally, wheat germ oil, octacosanol, flavor, and/or excipient. The method includes administering the composition to the mammal and, if the composition lacks wheat germ oil, also administering wheat germ oil to the mammal.

BACKGROUND OF THE INVENTION

Diabetes is prevalent in humans and other animals, such as companion animals. It is becoming increasingly prevalent in humans. Control of blood glucose levels can be achieved by administering insulin or other medications for type II diabetes. However, insulin or these other medications may not provide the desired or optimal control of blood glucose levels or can have significant negative side effects.

Canine diabetes can be a frustrating disease to manage. Insulin injections, dose regulation, dietary and treat restrictions, cataract development, excess thirst and frequent urination are a few of the issues that cause pet owners to become frustrated and give up treating their canine The owners of a diabetic dog have many demands placed upon their time and energies and many pets are unnecessarily euthanized. The many concerns people face are: cost of insulin, time and dedication to administering the insulin, and the need for adherence to a rigid schedule. In addition, once insulin administration begins, testing becomes a time consuming process, to regulate the insulin, with frequent visits to the veterinarian.

There remains a need for compositions that control blood glucose levels in mammals.

SUMMARY OF THE INVENTION

The present invention relates to a composition and method for reducing blood glucose levels in a mammal, such as a canine or human. The composition includes bran, cinnamon, yeast, gelatin, and optionally, wheat germ oil, octacosanol, flavor, and/or excipient. The method includes administering the composition to the mammal and, if the composition lacks wheat germ oil, also administering wheat germ oil to the mammal.

The present composition can include about 10 to about 45 wt-% yeast; about 10 to about 70 wt-% bran; about 2 to about 30 wt-% cinnamon; and about 5 to about 15 wt-% gelatin. This composition can also include about 5 to about 15 wt-% wheat germ oil; about 5 to about 30 wt-% flavoring; about 0.1 to about 2 wt-% octacosanol; about 0.5 to about 3 wt-% chromium enhanced yeast; or a plurality thereof.

The present method can include reducing a blood glucose level in a subject in need thereof by administering to the subject a composition comprising: about 10 to about 45 wt-% yeast; about 10 to about 70 wt-% bran; about 2 to about 30 wt-% cinnamon; and about 5 to about 15 wt-% gelatin. The composition administered can also include about 5 to about 15 wt-% wheat germ oil; about 5 to about 30 wt-% flavoring; about 0.1 to about 2 wt-% octacosanol; about 0.5 to about 3 wt-% chromium enhanced yeast; or a plurality thereof.

DETAILED DESCRIPTION OF THE INVENTION

Figure 1:
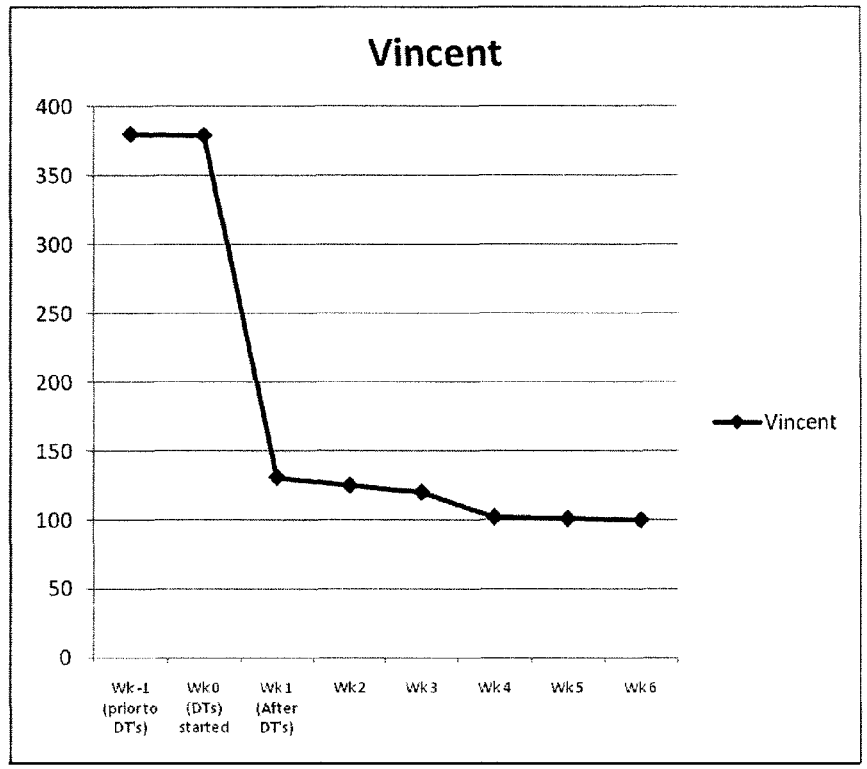
FIGS. 1, 2, 4, 6, 8, 10, 12, and 14-16 are graphs demonstrating that blood glucose levels in dogs decreased upon introduction of treatment with a composition of the present invention.
Figure 2:
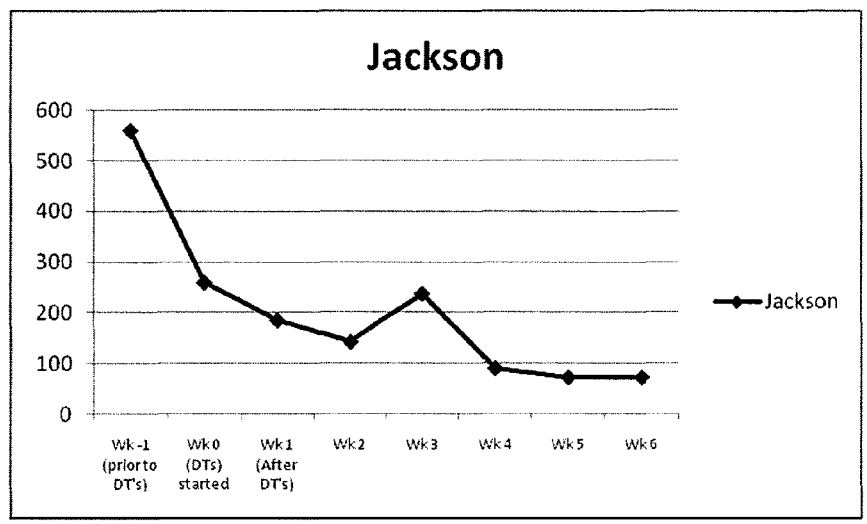
Figure 3:
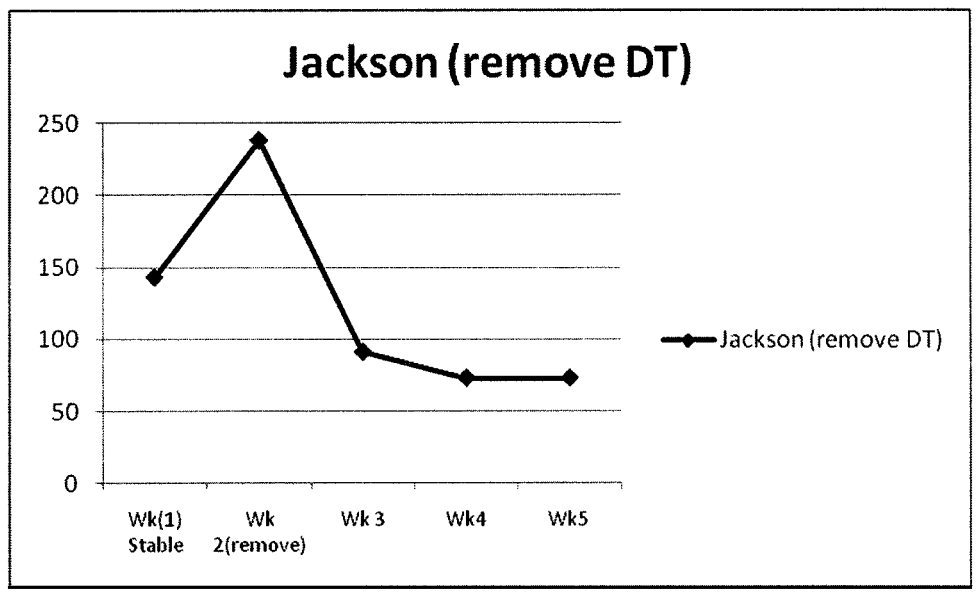
FIGS. 3, 5, 7, 9, 11, and 13 are graphs that illustrate that blood glucose levels in dogs increased upon withdrawing a composition of the present invention.
Figure 4:
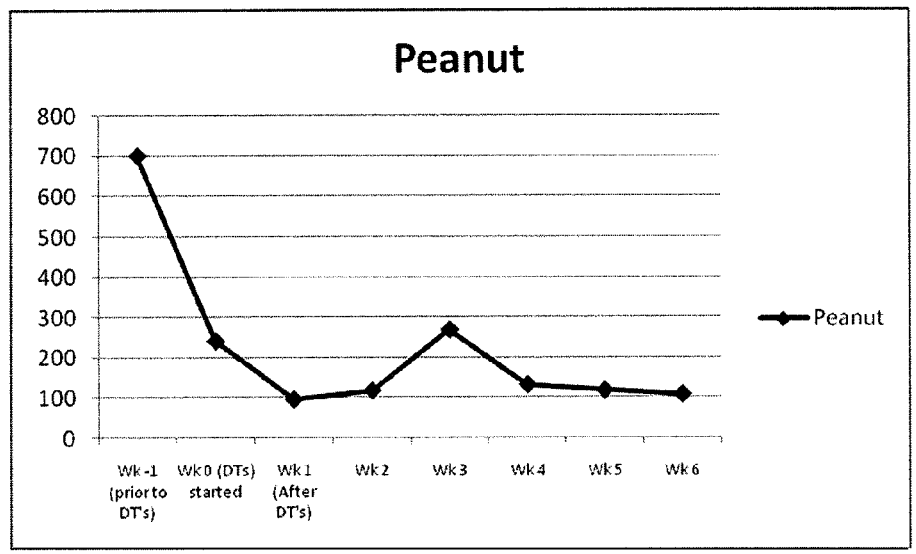
Figure 5:
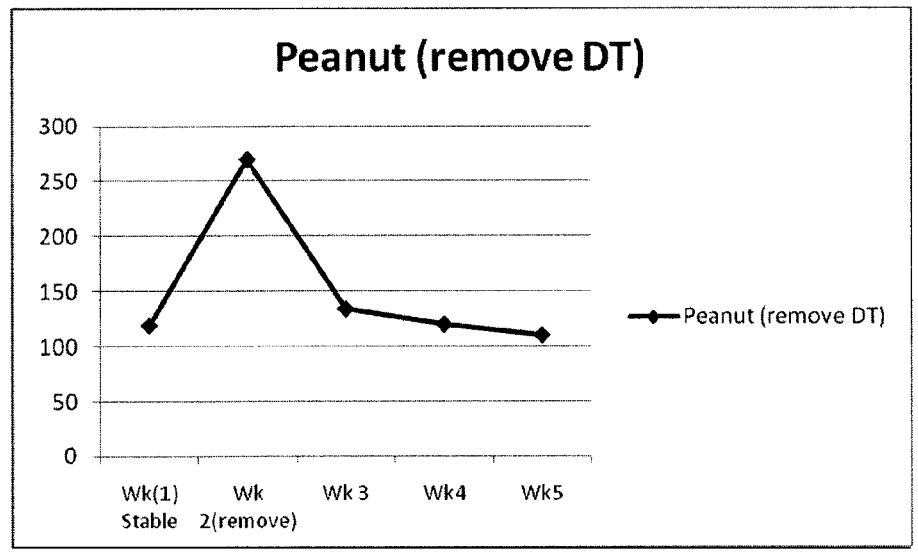
Figure 6:
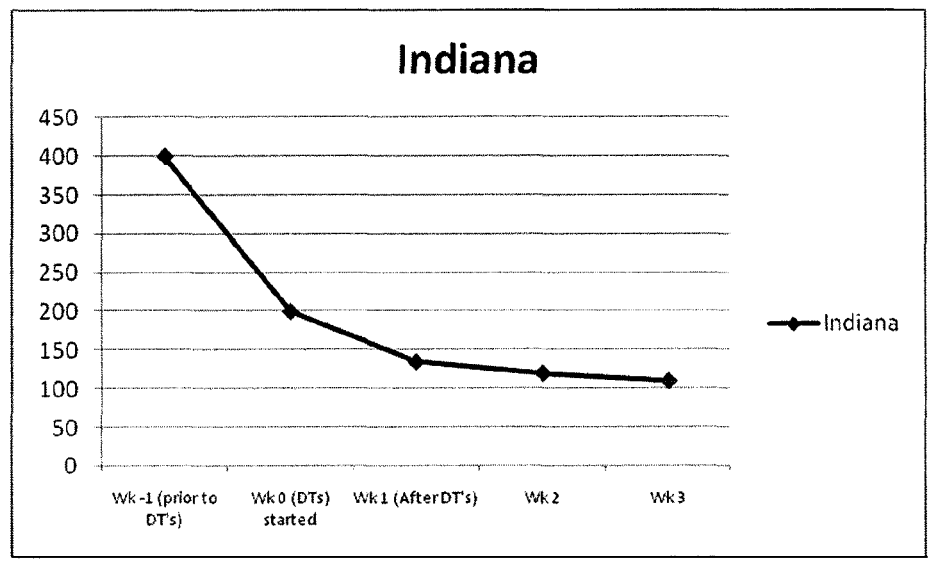
Figure 7:
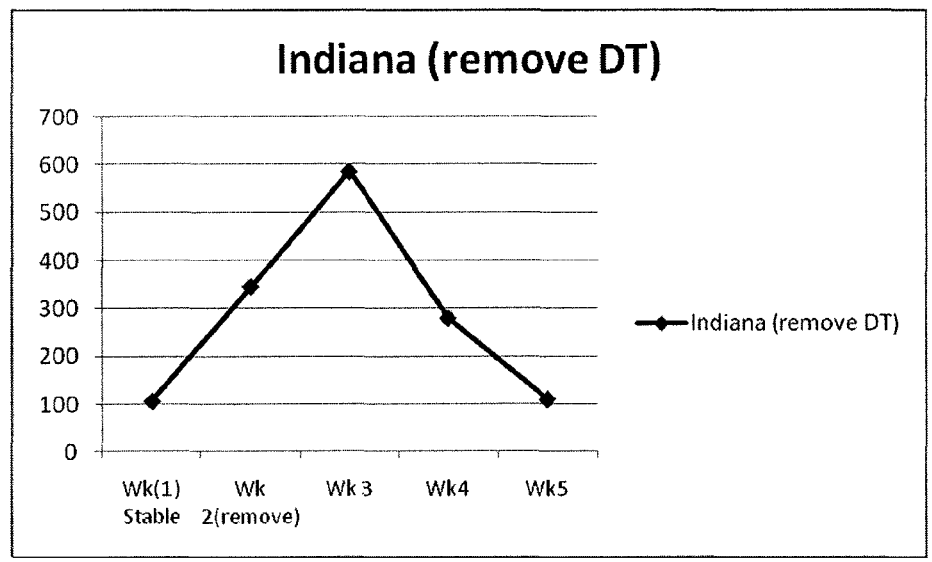
Figure 8:
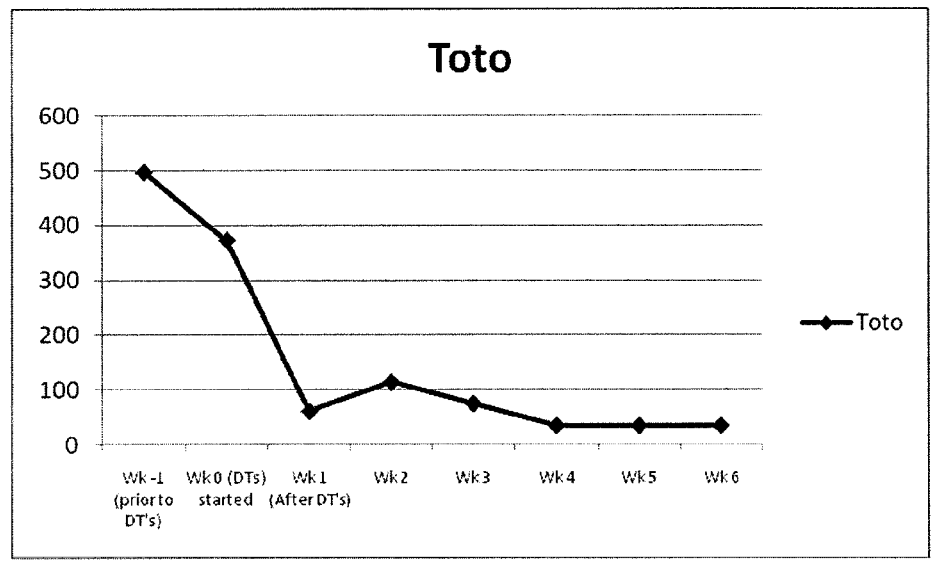
Figure 9:
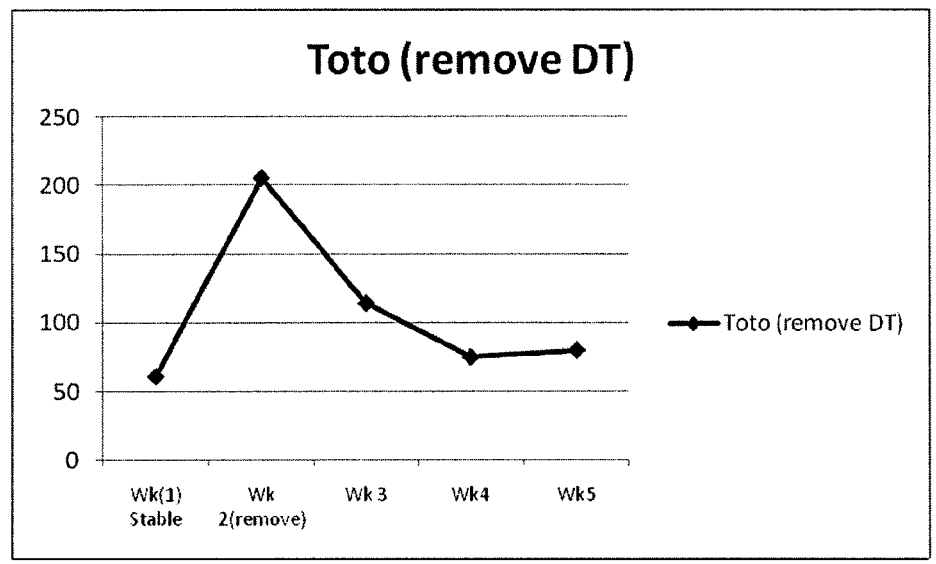
Figure 10:
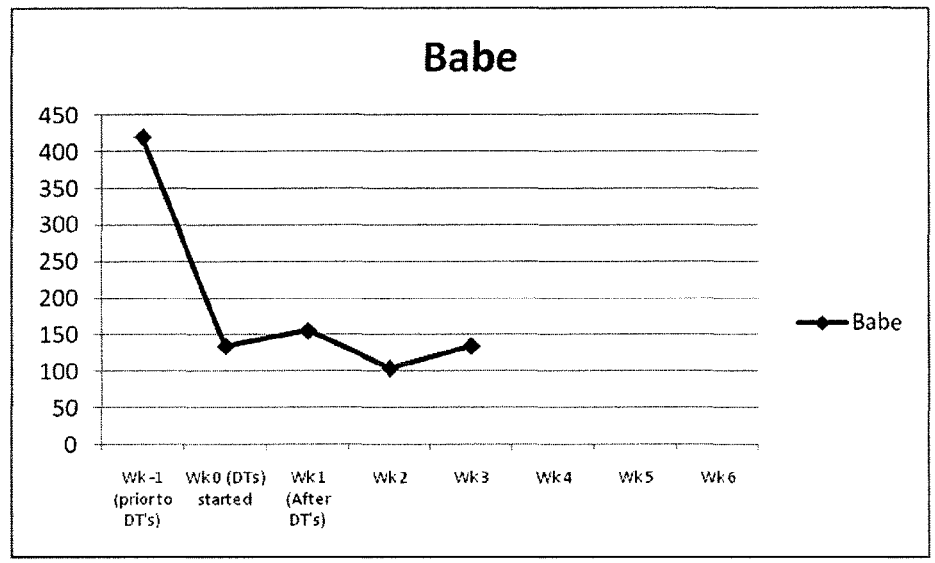
Figure 11:
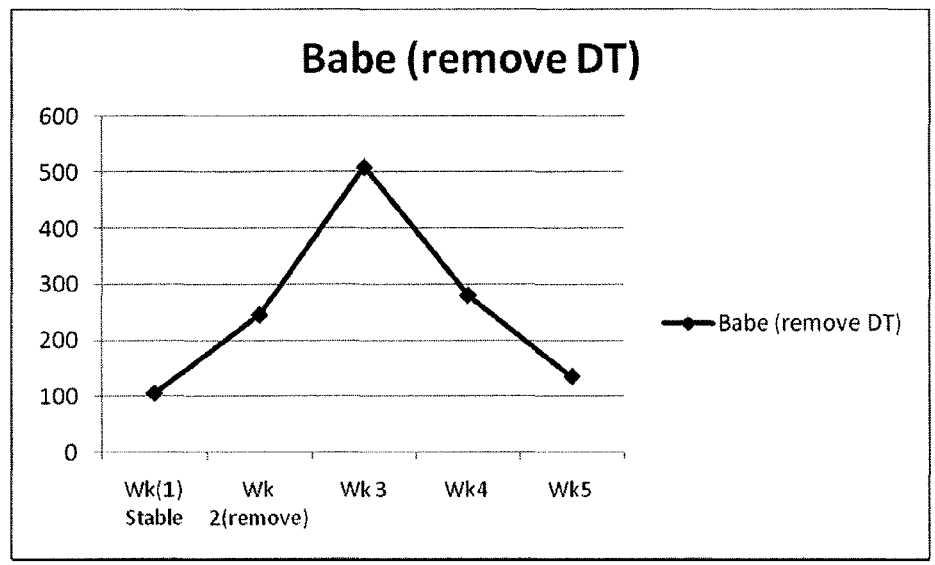
Figure 12:
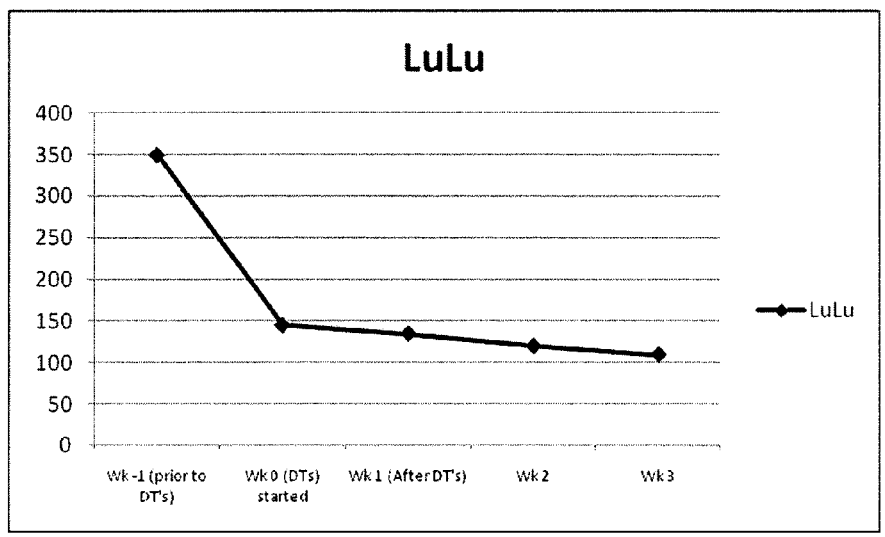
Figure 13:
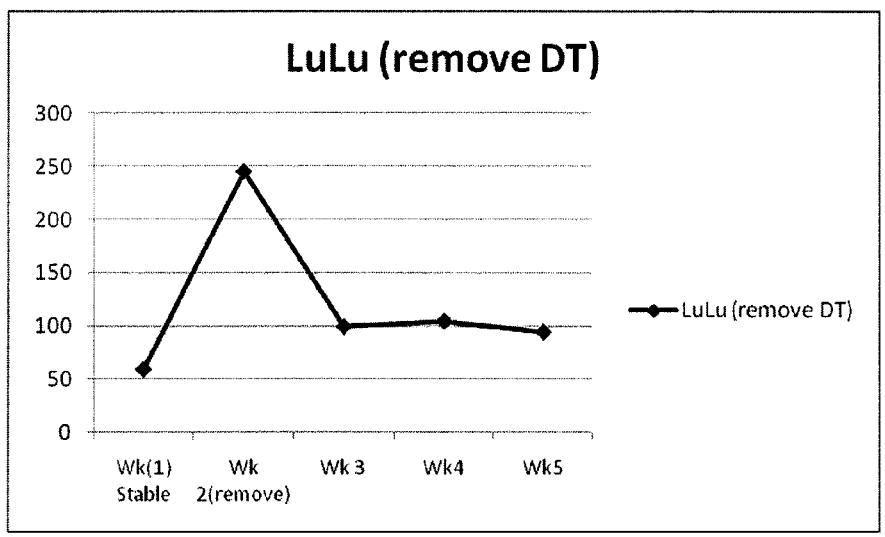
Figure 14:
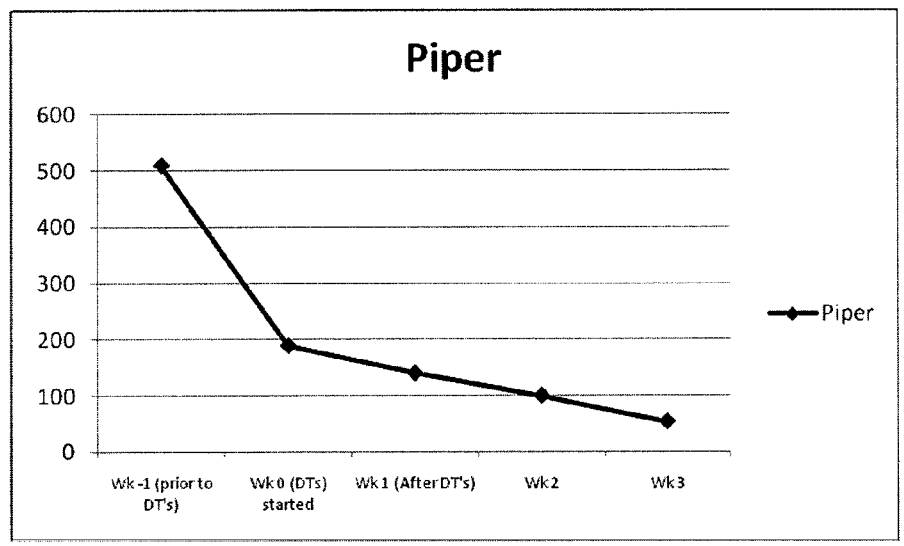
Figure 15:
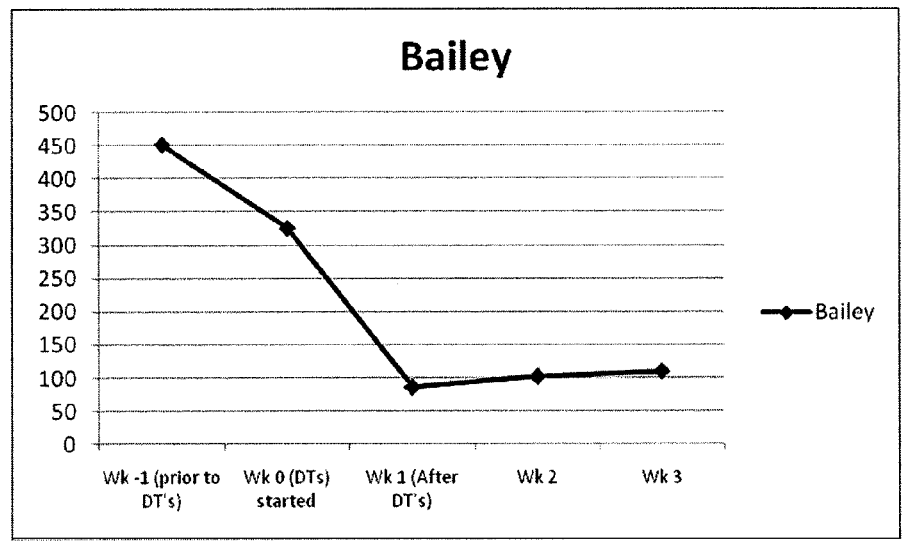
Figure 16:
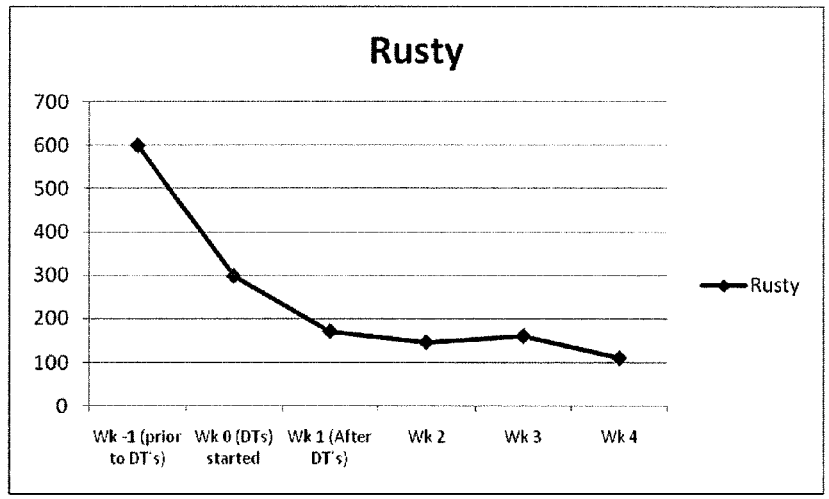

The present invention relates to a composition and method for reducing blood glucose levels in a mammal, such as a canine or human, in need thereof. The composition includes bran, cinnamon, yeast, gelatin, and optionally, wheat germ oil, octacosanol, flavor, and/or excipient. In an embodiment, the yeast is or includes brewers yeast. In an embodiment, the bran is or includes wheat bran and oat bran. In an embodiment, the ingredients of the composition are natural and nontoxic. The composition can be in edible form, such as a treat or kibble for a dog or a bar, wafer, cracker, or shake for a human.

The present method includes administering the composition to the mammal and, if the composition lacks wheat germ oil, also administering wheat germ oil to the mammal. The present composition has been proven to reduce blood glucose levels in mammals, such as humans and canines Embodiments of the composition have also been demonstrated to increase insulin sensitivity (e.g., lower the required dose of insulin for effective glucose control), stabilize blood glucose levels, and ameliorate other adverse effects associated with diabetes. In an embodiment, the present composition can reduce the dose of insulin or other medication required for effective control of glucose levels. In an embodiment, the present composition can ameliorate detrimental effects of diabetes, e.g., type I or type II diabetes. In an embodiment, the present composition can ameliorate detrimental effects of insulin resistance.

Embodiments of the Present Composition

In certain embodiments, the present composition can include (Table A):

| Ingredient | wt-% | wt-% | wt-% | wt-% | wt-% | wt-% |
|---|---|---|---|---|---|---|
| brewer's yeast | 10-45 | 15-40 | 20-35 | 33 | 19 | 22 |
| bran | 10-70 | 20-60 | 30-50 | 38 | 38 | 44 |
| cinnamon | 2-30 | 5-25 | 10-20 | 19 | 10 | 11 |

-continued

| Ingredient | wt-% | wt-% | wt-% | wt-% | wt-% | wt-% |
|---|---|---|---|---|---|---|
| wheat germ oil | 0 or 5-15 | 0 or 6-14 | 0 or 8-12 | | 10 | 11 |
| gelatin | 5-15 | 6-14 | 8-12 | 9 | 10 | 11 |
| flavoring | 0 or 5-30 | 0 or 10-25 | 0 or 15-20 | | 11 | |
| octacosanol | 0 or 0.1-2 | 0 or 0.2-1.5 | 0 or 0.3-1 | | | 1.6 |
| chromium enriched yeast | 0 or 0.5-3 | 0 or 0.7-2.5 | 0 or 1-2 | 1.6 | | |

These embodiments can include any of the amounts, ranges, or end points in the table modified by "about".

In certain embodiments, the present composition can include (Table B):

| Ingredient | wt-% | wt-% | wt-% | wt-% | wt-% | wt-% |
|---|---|---|---|---|---|---|
| brewer's yeast | 10-45 | 15-40 | 20-35 | 33 | 19 | 22 |
| bran, e.g., wheat bran | 5-35 | 10-30 | 15-25 | 19 | 19 | 22 |
| bran, e.g., oat bran | 5-35 | 10-30 | 15-25 | 19 | 19 | 22 |
| cinnamon | 2-30 | 5-25 | 10-20 | 19 | 10 | 11 |
| wheat germ oil | 0 or 5-15 | 0 or 6-14 | 0 or 8-12 | | 10 | 11 |
| gelatin | 5-15 | 6-14 | 8-12 | 9 | 10 | 11 |
| flavoring | 0 or 5-30 | 0 or 10-25 | 0 or 15-20 | | 11 | |
| octacosanol | 0 or 0.1-2 | 0 or 0.2-1.5 | 0 or 0.3-1 | | | 1.6 |
| chromium enriched yeast | 0 or 0.5-3 | 0 or 0.7-2.5 | 0 or 1-2 | 1.6 | | |

These embodiments can include any of the amounts, ranges, or end points in the table modified by "about".

In certain embodiments, the present composition can include (Table C):

| Ingredient | wt-% | wt-% | wt-% | wt-% |
|---|---|---|---|---|
| brewer's yeast | 18-35 | 20-25 | 21-23 | 22 |
| bran | 16-60 | 35-50 | 42-46 | 44 |
| cinnamon | 8-25 | 9-20 | 10-12 | 11 |
| wheat germ oil | 8-25 | 9-20 | 10-12 | 11 |
| gelatin | 4-17 | 6-14 | 10-12 | 11 |

These embodiments can include any of the amounts, ranges, or end points in the table modified by "about".

In certain embodiments, the present composition can include (Table D):

| Ingredient | wt-% | wt-% | wt-% | wt-% |
|---|---|---|---|---|
| brewer's yeast | 18-35 | 20-25 | 21-23 | 22 |
| bran, e.g., wheat bran | 8-30 | 20-25 | 21-23 | 22 |
| bran, e.g., oat bran | 8-30 | 20-25 | 21-23 | 22 |
| cinnamon | 8-25 | 9-20 | 10-12 | 11 |
| wheat germ oil | 8-25 | 9-20 | 10-12 | 11 |
| gelatin | 4-17 | 6-14 | 10-12 | 11 |

These embodiments can include any of the amounts, ranges, or end points in the table modified by "about".

In certain embodiments, the present composition can include (Table E):

| Ingredient | wt-% | wt-% | wt-% | wt-% |
|---|---|---|---|---|
| brewer's yeast | 15-30 | 15-25 | 18-20 | 19 |
| bran | 10-45 | 20-40 | 36-40 | 38 |
| cinnamon | 7-20 | 8-15 | 9-11 | 10 |
| wheat germ oil | 8-20 | 8-15 | 9-11 | 10 |
| gelatin | 3-15 | 5-12 | 9-11 | 10 |
| flavoring or excipient | 0 or 2-25 | 0 or 5-20 | 0 or 10-15 | 11 |
| octacosanol | 0 or 0.2-3 | 0 or 0.5-2.5 | 0 or 1-2 | 1.6 |

These embodiments can include any of the amounts, ranges, or end points in the table modified by "about".

In certain embodiments, the present composition can include (Table F):

| Ingredient | wt-% | wt-% | wt-% | wt-% |
|---|---|---|---|---|
| brewer's yeast | 15-30 | 15-25 | 18-20 | 19 |
| bran, e.g., wheat bran | 10-30 | 15-25 | 18-20 | 19 |
| bran, e.g., oat bran | 10-30 | 15-25 | 18-20 | 19 |
| cinnamon | 7-20 | 8-15 | 9-11 | 10 |
| wheat germ oil | 8-20 | 8-15 | 9-11 | 10 |
| gelatin | 3-15 | 5-12 | 9-11 | 10 |
| flavoring | 0 or 2-25 | 0 or 5-20 | 0 or 10-15 | 11 |
| octacosanol | 0 or 0.2-3 | 0 or 0.5-2.5 | 0 or 1-2 | 1.6 |

These embodiments can include any of the amounts, ranges, or end points in the table modified by "about".

In certain embodiments, the present composition can include (Table G):

| Ingredient | wt-% | wt-% | wt-% | wt-% |
|---|---|---|---|---|
| brewer's yeast | 29-50 | 31-40 | 32-34 | 33 |
| bran (e.g., powder) | 14-44 | 30-44 | 36-40 | 38 |
| cinnamon | 15-40 | 16-30 | 18-20 | 19 |
| gelatin | 2-15 | 4-12 | 8-10 | 9 |
| chromium enriched yeast | 0.8-3 | 1-2.5 | 1.5-1.7 | 1.6 |

These embodiments can include any of the amounts, ranges, or end points in the table modified by "about".

In certain embodiments, the present composition can include (Table H):

| Ingredient | wt-% | wt-% | wt-% | wt-% |
|---|---|---|---|---|
| brewer's yeast | 29-50 | 31-40 | 32-34 | 33 |
| bran, e.g., wheat bran powder | 7-22 | 15-22 | 18-20 | 19 |
| bran, e.g., oat bran powder | 7-22 | 15-22 | 18-20 | 19 |
| cinnamon | 15-40 | 16-30 | 18-20 | 19 |
| gelatin | 2-15 | 4-12 | 8-10 | 9 |
| chromium enriched yeast | 0.8-3 | 1-2.5 | 1.5-1.7 | 1.6 |

These embodiments can include any of the amounts, ranges, or end points in the table modified by "about".

In certain embodiments, the present composition can include (Table I):

| Ingredient | wt-% | wt-% | wt-% | wt-% | wt-% |
|---|---|---|---|---|---|
| brewer's yeast | 2-35 | 5-25 | 10-15 | 12 | 14 |
| bran | 5-60 | 10-40 | 20-30 | 24 | 28 |
| cinnamon | 1-20 | 2-15 | 5-10 | 6 | 7 |

-continued

| Ingredient | wt-% | wt-% | wt-% | wt-% | wt-% |
|---|---|---|---|---|---|
| wheat germ oil | 1-20 | 2-15 | 5-10 | 6 | 7 |
| gelatin | 1-20 | 2-15 | 5-10 | 6 | 7 |
| water | 20-60 | 30-45 | 35-40 | 38 | 37 |
| flavoring | 0 or 2-30 | 0 or 5-20 | 0 or 10-15 | 7 | |
| octacosanol | 0 or 0.1-2 | 0 or 0.2-1 | 0 or 0.3-0.5 | 1 | |

These embodiments can include any of the amounts, ranges, or end points in the table modified by "about".

In certain embodiments, the present composition can include (Table J):

| Ingredient | wt-% | wt-% | wt-% | wt-% | wt-% |
|---|---|---|---|---|---|
| brewer's yeast | 2-35 | 5-25 | 10-15 | 12 | 14 |
| bran, e.g., wheat bran | 2-35 | 5-25 | 10-15 | 12 | 14 |
| bran, e.g., oat bran | 2-35 | 5-25 | 10-15 | 12 | 14 |
| cinnamon | 1-20 | 2-15 | 5-10 | 6 | 7 |
| wheat germ oil | 1-20 | 2-15 | 5-10 | 6 | 7 |
| gelatin | 1-20 | 2-15 | 5-10 | 6 | 7 |
| water | 20-60 | 30-45 | 35-40 | 38 | 37 |
| flavoring | 0 or 2-30 | 0 or 5-20 | 0 or 10-15 | 7 | |
| octacosanol | 0 or 0.1-2 | 0 or 0.2-1 | 0 or 0.3-0.5 | 1 | |

These embodiments can include any of the amounts, ranges, or end points in the table modified by "about".

In certain embodiments, the present composition can include (Table K):

| Ingredient | wt-% | wt-% | wt-% | wt-% |
|---|---|---|---|---|
| brewer's yeast | 10-25 | 11-20 | 13-15 | 14 |
| bran | 20-50 | 23-40 | 26-30 | 28 |
| cinnamon | 4-25 | 5-15 | 6-8 | 7 |
| wheat germ oil | 4-25 | 5-15 | 6-8 | 7 |
| gelatin | 3-17 | 5-12 | 6-8 | 7 |
| water | 20-50 | 30-45 | 35-40 | 37 |

These embodiments can include any of the amounts, ranges, or end points in the table modified by "about".

In certain embodiments, the present composition can include (Table L):

| Ingredient | wt-% | wt-% | wt-% | wt-% |
|---|---|---|---|---|
| brewer's yeast | 10-25 | 11-20 | 13-15 | 14 |
| bran, e.g., wheat bran | 10-25 | 11-20 | 13-15 | 14 |
| bran, e.g., oat bran | 10-25 | 11-20 | 13-15 | 14 |
| cinnamon | 4-25 | 5-15 | 6-8 | 7 |
| wheat germ oil | 4-25 | 5-15 | 6-8 | 7 |
| gelatin | 3-17 | 5-12 | 6-8 | 7 |
| water | 20-50 | 30-45 | 35-40 | 37 |

These embodiments can include any of the amounts, ranges, or end points in the table modified by "about".

In certain embodiments, the present composition can include (Table M):

| Ingredient | wt-% | wt-% | wt-% | wt-% |
|---|---|---|---|---|
| brewer's yeast | 9-20 | 10-15 | 13-14 | 12 |
| bran | 5-35 | 10-30 | 22-26 | 24 |
| cinnamon | 4-15 | 5-10 | 5-7 | 6 |
| wheat germ oil | 5-15 | 5-10 | 5-7 | 6 |
| gelatin | 3-15 | 5-10 | 5-7 | 6 |
| water | 20-50 | 30-45 | 35-40 | 38 |
| flavoring or excipient | 0 or 3-20 | 0 or 4-15 | 0 or 5-10 | 7 |
| octacosanol | 0 or 0.2-2 | 0 or 0.5-1.5 | 0 or 0.9-1.1 | 1 |

These embodiments can include any of the amounts, ranges, or end points in the table modified by "about".

In certain embodiments, the present composition can include (Table N):

| Ingredient | wt-% | wt-% | wt-% | wt-% |
|---|---|---|---|---|
| brewer's yeast | 9-20 | 10-15 | 12-13 | 12 |
| bran, e.g., wheat bran | 2-20 | 5-15 | 12-13 | 12 |
| bran, e.g., oat bran | 2-20 | 5-15 | 12-13 | 12 |
| cinnamon | 4-15 | 5-10 | 5-7 | 6 |
| wheat germ oil | 5-15 | 5-10 | 5-7 | 6 |
| gelatin | 3-15 | 5-10 | 5-7 | 6 |
| water | 20-50 | 30-45 | 35-40 | 38 |
| flavoring or excipient | 0 or 3-20 | 0 or 5-15 | 0 or 10-12 | 7 |
| octacosanol | 0 or 0.1-2 | 0 or 0.2-1 | 0 or 0.3-0.5 | 1 |

These embodiments can include any of the amounts, ranges, or end points in the table modified by "about".

In certain embodiments, the present composition can include (Table O):

| Ingredient | wt-% | wt-% | wt-% | wt-% | wt-% | wt-% |
|---|---|---|---|---|---|---|
| brewer's yeast | 10-50 | 15-45 | 20-40 | 36 | 21 | 24 |
| bran | 20-70 | 30-60 | 40-50 | 42 | 42 | 48 |
| cinnamon | 2-30 | 5-25 | 10-20 | 21 | 11 | 12 |
| wheat germ oil | 0 or 5-15 | 0 or 6-14 | 0 or 10-13 | | 11 | 12 |
| flavoring | 0 or 2-25 | 0 or 5-20 | 0 or 10-15 | | 12 | |
| octacosanol | 0 or 0.2-3 | 0 or 0.5-2.5 | 0 or 1-2 | | 1.6 | |
| chromium enriched yeast | 0 or 0.5-3.5 | 0 or 0.7-3 | 0 or 1.5-2.5 | 1.8 | | |

These embodiments can include any of the amounts, ranges, or end points in the table modified by "about".

In certain embodiments, the present composition can include (Table P):

| Ingredient | wt-% | wt-% | wt-% | wt-% | wt-% | wt-% |
|---|---|---|---|---|---|---|
| brewer's yeast | 10-50 | 15-45 | 20-40 | 36 | 21 | 24 |
| bran, e.g., wheat bran | 10-35 | 15-30 | 20-25 | 19 | 21 | 22 |
| bran, e.g., oat bran | 10-35 | 15-30 | 20-25 | 19 | 21 | 22 |
| cinnamon | 2-30 | 5-25 | 10-20 | 21 | 11 | 12 |

-continued

| Ingredient | wt-% | wt-% | wt-% | wt-% | wt-% | wt-% |
|---|---|---|---|---|---|---|
| wheat germ oil | 0 or 5-15 | 0 or 6-14 | 0 or 10-13 | | 11 | 12 |
| flavoring | 0 or 2-25 | 0 or 5-20 | 0 or 10-15 | | | 12 |
| octacosanol | 0 or 0.2-3 | 0 or 0.5-2.5 | 0 or 1-2 | | | 1.6 |
| chromium enriched yeast | 0 or 0.5-3.5 | 0 or 0.7-3 | 0 or 1.5-2.5 | 1.8 | | |

These embodiments can include any of the amounts, ranges, or end points in the table modified by "about".

In certain embodiments, the present composition can include (Table Q):

| Ingredient | wt-% | wt-% | wt-% | wt-% |
|---|---|---|---|---|
| brewer's yeast | 18-35 | 20-30 | 23-25 | 24 |
| bran | 16-60 | 35-55 | 46-50 | 48 |
| cinnamon | 8-25 | 9-20 | 11-13 | 12 |
| wheat germ oil | 8-25 | 9-20 | 11-13 | 12 |

These embodiments can include any of the amounts, ranges, or end points in the table modified by "about".

In certain embodiments, the present composition can include (Table R):

| Ingredient | wt-% | wt-% | wt-% | wt-% |
|---|---|---|---|---|
| brewer's yeast | 18-35 | 20-30 | 23-25 | 24 |
| bran, e.g., wheat bran | 8-30 | 20-30 | 23-25 | 24 |
| bran, e.g., oat bran | 8-30 | 20-30 | 23-25 | 24 |
| cinnamon | 8-25 | 9-20 | 11-13 | 12 |
| wheat germ oil | 8-25 | 9-20 | 11-13 | 12 |

These embodiments can include any of the amounts, ranges, or end points in the table modified by "about".

In certain embodiments, the present composition can include (Table S):

| Ingredient | wt-% | wt-% | wt-% | wt-% |
|---|---|---|---|---|
| brewer's yeast | 10-30 | 15-25 | 20-22 | 21 |
| bran | 25-60 | 35-50 | 40-44 | 42 |
| cinnamon | 7-20 | 8-15 | 10-12 | 11 |
| wheat germ oil | 7-20 | 8-15 | 10-12 | 11 |
| flavoring or excipient | 0 or 2-25 | 0 or 5-20 | 0 or 10-15 | 12 |
| octacosanol | 0 or 0.2-3 | 0 or 0.5-2.5 | 0 or 1-2 | 1.6 |

These embodiments can include any of the amounts, ranges, or end points in the table modified by "about".

In certain embodiments, the present composition can include (Table T):

| Ingredient | wt-% | wt-% | wt-% | wt-% |
|---|---|---|---|---|
| brewer's yeast | 10-30 | 15-25 | 20-22 | 21 |
| bran, e.g., wheat bran | 10-30 | 15-25 | 20-22 | 21 |
| bran, e.g., oat bran | 10-30 | 15-25 | 20-22 | 21 |
| cinnamon | 7-20 | 8-15 | 10-12 | 11 |
| wheat germ oil | 7-20 | 8-15 | 10-12 | 11 |
| flavoring or excipient | 0 or 2-25 | 0 or 5-20 | 0 or 10-15 | 12 |
| octacosanol | 0 or 0.2-3 | 0 or 0.5-2.5 | 0 or 1-2 | 1.6 |

These embodiments can include any of the amounts, ranges, or end points in the table modified by "about".

In certain embodiments, the present composition can include (Table U):

| Ingredient | wt-% | wt-% | wt-% | wt-% |
|---|---|---|---|---|
| brewer's yeast | 30-50 | 31-40 | 35-37 | 36 |
| bran (e.g., powder) | 20-48 | 30-46 | 40-44 | 42 |
| cinnamon | 15-40 | 16-30 | 20-22 | 21 |
| chromium enriched yeast | 0.8-3 | 1-2.5 | 1.5-1.7 | 1.8 |

These embodiments can include any of the amounts, ranges, or end points in the table modified by "about".

In certain embodiments, the present composition can include (Table V):

| Ingredient | wt-% | wt-% | wt-% | wt-% |
|---|---|---|---|---|
| brewer's yeast | 30-50 | 31-40 | 35-37 | 36 |
| bran, e.g., wheat bran powder | 10-24 | 15-23 | 20-22 | 21 |
| bran, e.g., oat bran powder | 10-24 | 15-23 | 20-22 | 21 |
| cinnamon | 15-40 | 16-30 | 20-22 | 21 |
| chromium enriched yeast | 0.8-3 | 1-2.5 | 1.5-1.7 | 1.8 |

These embodiments can include any of the amounts, ranges, or end points in the table modified by "about".

In certain embodiments, the present composition can include (Table W):

| Ingredient | Relative Amount | Relative Amount | Relative Amount | Relative Amount | Relative Amount | Relative Amount |
|---|---|---|---|---|---|---|
| brewer's yeast | 0.7-1.5 | 0.7-1.5 | 0.7-1.5 | 1 | 1 | 1 |
| bran | 0.9-1.8 | 1.5-2.5 | 1.5-2.5 | 1.2 | 2 | 2 |
| cinnamon | 0.4-0.9 | 0.3-0.7 | 0.7-1.5 | 0.6 | 0.5 | 1 |
| wheat germ oil | | 0.3-0.7 | 0.7-1.5 | | 0.5 | 1 |
| gelatin | 0.2-0.4 | 0.3-0.7 | 0.7-1.5 | 0.3 | 0.5 | 1 |
| flavoring | | 0.7-1.5 | | | 1 | |
| octacosanol | | 0.03-0.06 | | | 0.04 | |
| chromium enriched yeast | 0.03-0.07 | | | 0.05 | | |

The relative amounts are relative only to those in the same column.

The composition can be in any of a variety of forms. A composition including water (e.g., as listed above) can be in the form of a moist, set but not hard, mass. The composition including water can be provided in a packet or other container. The packet can be a unit dose. The container can include numerous doses of the composition and a scoop or other measuring device to dispense an appropriate single dose. An appropriate amount of the composition including water can be consumed as a dose by a mammal. An appropriate amount (dose) of the composition including water can be a treat for a dog. An appropriate amount (dose) of the composition including water can be consumed by a human. An appropriate amount (dose) of the composition including water can be mixed with food or beverage before administering. For example, the composition including water can be a component of a bar (e.g., a nutritional bar) or a shake (e.g., a nutritional shake). For example, the composition including water can be mixed with a food or beverage before consuming the food or beverage.

The composition can be in the form of a powder. For example, a composition that lacks wheat germ oil and water (e.g., as listed above) can be in the form of a powder. The powder can be in a capsule. The powder can be provided in a packet. An appropriate amount of the powder composition can be consumed as a dose by a mammal. A packet, for example could be a unit dose. A container can include numerous doses of the powder and a scoop or other measuring device to dispense an appropriate single dose. The powder can be mixed with food or beverage before administering. For example, the powder can be a component of a bar (e.g., a nutritional bar) or a shake (e.g., a nutritional shake). For example, the powder can be mixed with a food or beverage before consuming the food or beverage. A composition lacking wheat germ oil can be consumed with a separate dose of wheat germ oil. Or, the wheat germ oil can be a component of or mixed into the food or beverage that also contains the present composition.

In an embodiment, the present composition includes: about 10 to about 45 wt-% yeast; about 10 to about 70 wt-% bran; about 2 to about 30 wt-% cinnamon; and about 5 to about 15 wt-% gelatin. This embodiment of the composition can also include: about 5 to about 15 wt-% wheat germ oil; about 5 to about 30 wt-% flavoring; about 0.1 to about 2 wt-% octacosanol; about 0.5 to about 3 wt-% chromium enhanced yeast; or a plurality thereof.

In an embodiment, the bran comprises approximately equal amounts of wheat bran and oat bran. In an embodiment, the yeast comprises brewers yeast, chromium enhanced yeast, or a mixture thereof; or a plurality thereof.

In an embodiment, the present composition includes about 22 wt-% brewers yeast; about 44 wt-% bran; about 11 wt-% cinnamon; about 11 wt-% gelatin; and about 11 wt-% wheat germ oil.

In an embodiment, the present composition includes about 17 wt-% brewers yeast; about 34 wt-% bran; about 9 wt-% cinnamon; about 9 wt-% gelatin; about 9 wt-% wheat germ oil; about 17 wt-% flavoring; and about 0.7 wt-% octacosanol.

In an embodiment, the present composition includes about 33 wt-% brewers yeast; about 38 wt-% bran; about 19 wt-% cinnamon; about 9 wt-% gelatin; and about 1.6 wt-% chromium enhanced yeast.

In certain embodiments, the present composition consists essentially of the listed ingredients. In certain embodiments, the present composition consists of the listed ingredients.

In an embodiment, for making a shake, the present composition includes: about 25 to about 30 (e.g., about 27) wt-% yeast; about 30 to about 35 (e.g., about 32) wt-% bran (e.g., bran powder); about 10 to about 20 (e.g., about 16) wt-% cinnamon; and about 5 to about 10 (e.g., about 8) wt-% gelatin. This embodiment of the composition can also include: about 5 to about 15 (e.g., about 11) wt-% flavoring (e.g., cacao and stevia); about 0.1 to about 2 wt-% octacosanol; about 0.5 to about 1.5 (e.g., about 1) wt-% chromium enhanced yeast; or a plurality thereof. This composition can be mixed with a beverage, for example water or milk for administering. If the composition lacks wheat germ oil, the wheat germ oil can be added to the beverage in an appropriate amount or consumed separately.

In an embodiment, for making a treat, the present composition includes: about 20 to about 30 (e.g., about 25) wt-% yeast; about 45 to about 55 (e.g., about 50) wt-% bran (e.g., bran flakes); about 10 to about 15 (e.g., about 13) wt-% cinnamon; and about 10 to about 15 (e.g., about 13) wt-% gelatin. These dry ingredients can be provided in a container (e.g., a tub or canister) together with a premeasured scoop. This composition can be mixed with water and wheat germ oil to make a treat. The wheat germ oil can be provided in a second container with the present composition.

In an embodiment, the gelatin is optional or the composition lacks gelatin.

Doses of and Methods of Administering the Present Composition

The compositions can be administered to a mammal in an amount effective to reduce blood glucose levels, e.g., to acceptable levels. The method of the present invention can include administering the present composition to a mammal in an amount effective to reduce blood glucose levels, e.g., to acceptable levels. The method can include administering a dose, e.g., an effective dose, of the present composition. The method can also include administering wheat germ oil, for an embodiment of the present composition lacking wheat germ oil. The method can include administering one or more unit doses of the present composition. The unit dose can be, for example, a treat or kibble for a dog or a bar, wafer, cracker, or shake for a human. The dose can be a powder that can be consumed directly, mixed with food, or mixed with (e.g., suspended in) a fluid, for example, to make a shake.

In certain embodiments, a dose can be about 5 grams to about 60 grams of the present composition, which dose can be administered once, twice, or three times daily. In certain embodiments, a dose can be about 0.3 gram or 1 gram of the present composition per kilogram of body weight, about 0.1 to about 2 g/kg, about 0.2 to about 3 g/kg, or about 0.05 to about 5 g/kg. Such a dose can be administered once, twice, or three times daily. In certain embodiments, a dose can be about 5 to about 150 grams of the present composition per day, about 20 to about 90 grams per day, or about 30 to 60 grams per day.

In certain embodiments, for a human, a dose of the present composition can be about 5 grams to about 60 grams, about 10 grams to about 50 grams, or about 15 to about 30 grams which dose can be administered once, twice, or three times daily. In certain embodiments, for a human, a dose can be about 0.3 gram of the present composition per kilogram of body weight, about 0.2 to about 1 g/kg, about 0.1 to about 2 g/kg, or about 0.05 to about 5 g/kg. Such a dose can be administered once, twice, or three times daily. In certain embodiments, for an adult human, a dose can be about 5 to about 150 grams of the present composition per day, about 10 to about 90 grams per day, or about 20 to 60 grams per day.

In certain embodiments, for a human, a dose of the present composition can be about 2 grams to about 20 grams, which dose can be administered once, twice, or three times daily. If the embodiment of the present composition lacks wheat germ oil, wheat germ oil can be administered also. A suitable dose of wheat germ oil can be about 0.3 to about 3 grams (e.g., 1 gram), which can be administered once, twice, or three times daily. In certain embodiments, for a human, a dose can be about 0.1 gram of the present composition per kilogram of body weight, about 0.05 to about 0.2 g/kg, about 0.03 to about 0.3 g/kg, or about 0.01 to about 1 g/kg, which dose can be administered once, twice, or three times daily. If the embodiment of the present composition lacks wheat germ oil, wheat germ oil can be administered also. A suitable dose of wheat germ oil can be about 0.05 to about 2 g/kg, which can be administered once, twice, or three times daily. In certain embodiments, for an adult human, a dose can be about 5 to about 80 grams of the present composition per day, about 10 to about 40 grams per day, or about 15 to 25 grams per day. If the embodiment of the present composition lacks wheat germ oil, wheat germ oil can be administered also. A suitable dose of wheat germ oil can be about 1 to about 5 grams per day.

In certain embodiments, for a dog, a dose of the present composition can be about 5 grams to about 45 grams, which dose can be administered once, twice, or three times daily.

In certain embodiments, for a dog, a dose can be about 1 gram of the present composition per kilogram of body weight, about 0.5 to about 2 g/kg, about 0.3 to about 3 g/kg, or about 0.2 to about 5 g/kg. Such a dose can be administered once, twice, or three times daily. In certain embodiments, for a dog, a dose can be about 10 grams to about 100 grams of the present composition per day, about 5 to about 20 grams per day, about 15 to about 60 grams per day, or about 25 to about 100 grams per day.

For a dog, a dose can be administered in the form of a treat, which can be about one inch by one inch or one inch in diameter. The composition can be supplied as a composition in a container and the dose measured with a scoop. The composition can be provided as a powder in a container with a premeasured scoop and wheat germ oil can be provided also.

In an embodiment, the present method includes or is a method of reducing a blood glucose level in a subject in need thereof. This method can include administering to the subject a composition including: about 10 to about 45 wt-% yeast; about 10 to about 70 wt-% bran; about 2 to about 30 wt-% cinnamon; and about 5 to about 15 wt-% gelatin.

In an embodiment of the method, the subject also receives, takes, self administers, or is administered insulin to control the blood glucose level. In an embodiment of the method, the subject also receives insulin to control the blood glucose level. In an embodiment of the method, the subject also takes insulin to control the blood glucose level. In an embodiment of the method, the subject also self administers insulin to control the blood glucose level. In an embodiment of the method, the subject also is administered insulin to control the blood glucose level.

In certain embodiments, the present method includes administering the composition two hours, one hour, 30 minutes, or 15 minutes before a dose of insulin. In an embodiment, the present method includes administering the composition two hours, one hour, 30 minutes, or 15 minutes before a meal.

In an embodiment, the composition administered also includes about 5 to about 15 wt-% wheat germ oil; about 5 to about 30 wt-% flavoring; about 0.1 to about 2 wt-% octacosanol; about 0.5 to about 3 wt-% chromium enhanced yeast; or a plurality thereof.

In an embodiment, the present method includes administering a composition in which the bran comprises approximately equal amounts of wheat bran and oat bran.

In an embodiment, the present method includes administering a composition in which the yeast comprises brewers yeast, chromium enhanced yeast, or a plurality thereof.

This method can include administering to the subject a composition including: about 22 wt-% brewers yeast; about 44 wt-% bran; about 11 wt-% cinnamon; about 11 wt-% gelatin; and about 11 wt-% wheat germ oil.

This method can include administering to the subject a composition including: about 17 wt-% brewers yeast; about 34 wt-% bran; about 9 wt-% cinnamon; about 9 wt-% gelatin; about 9 wt-% wheat germ oil; about 17 wt-% flavoring; and about 0.7 wt-% octacosanol.

This method can include administering to the subject a composition including: about 33 wt-% brewers yeast; about 38 wt-% bran; about 19 wt-% cinnamon; about 9 wt-% gelatin; and about 1.6 wt-% chromium enhanced yeast.

The method can include orally administering the present composition.

The present composition can be in the form of a capsule containing an embodiment of the present composition lacking wheat germ oil and another capsule containing wheat germ oil. The present composition can be in the form of a dose of an embodiment of the present composition lacking wheat germ oil and a dose of wheat germ oil. An embodiment of the present composition lacking wheat germ oil can be provided with instructions instructing the subject to take or administer wheat germ oil (e.g., an dose or effective dose of wheat germ oil) with the present composition. For example, the present composition can be component of a kit or package containing the instructions and an embodiment of the present composition lacking wheat germ oil and.

Mammals that can benefit from the present composition or method include humans, mammalian companion animals (e.g., pets), and other domesticated mammals (e.g., livestock). Companion animals that can benefit from the present composition or method include dogs, cats, rabbits, and rodents. In an embodiment, the mammal is a human or a dog. In an embodiment, the mammal is a cat or a dog. In an embodiment, the mammal is a human. In an embodiment, the mammal is a dog. In an embodiment, the mammal is a cat.

Although not limiting to the present invention, it is believed that, in an embodiment, the present composition and method can contribute to stabilizing blood glucose in a normal range and reduce the degree of fluctuations in blood glucose levels. In an embodiment, the present composition and method stabilize blood glucose level.

Ingredients for the Present Composition

The present composition can include yeast (e.g., brewers yeast), bran (e.g., wheat and/or oat bran), cinnamon, gelatin, and optionally, wheat germ oil, octacosanol, flavor, and/or excipient or filler. The ingredients are commercially available.

Suitable yeast includes brewer's yeast, chromium enhanced yeast, nutritional yeast, or a mixture thereof. An embodiment of brewer's yeast is yeast suitable for fermenting sugars to alcohol in the brewing of, for example, beer, and can be *Saccharomyces cerevisiae*. In an embodiment, brewers yeast includes, for example, folic acid, amino acids, biotin, chromium, selenium, manganese, potassium. In an embodiment, brewers yeast includes, for example, all of the essential amino acids, 14 minerals, and 17 vitamins. In an embodiment, brewers yeast includes, for example, one or more of the B-complex vitamins thiamin, riboflavin, niacin, B6, pantothenic acid, biotin, folic acid, or a mixture thereof. In an embodiment, brewers yeast includes, for example, chromium, zinc, iron, phosphorus, magnesium, manganese, and selenium. In an embodiment, brewers yeast includes, for example, contains approximately 16 g of protein per 30 g of powdered yeast. In an embodiment, two tablespoons of brewer's yeast yields about 120 micrograms (µg) of chromium, an amount equal to the recommended daily allowance. The brewer's yeast can be in any of a variety of commercially available forms (e.g., tablet, flake, or powder) for use in or for making the present composition.

Chromium enriched yeast is a yeast that has been grown in the presence of or otherwise supplemented with ionic chromium (e.g., trivalent chromium). In an embodiment, chromium enriched yeast includes inactivated dried whole cell yeast (*Saccharomyces cerevisiae*) containing elevated levels of chromium. It can be prepared through a yeast fermentation supplemented with low levels of trivalent chromium. The yeast cream can be pasteurized and then spray dried or roller-dried/grinded. Such chromium enhanced yeast can include 2000-2400 μg Chromium per gram of the yeast preparation.

Although not limiting to the present invention, it is believed that a composition including brewers yeast is more effective at lowering mammalian blood glucose levels than, for example, a composition including as the only yeast bakers yeast.

The present composition includes bran, such as bran of a cereal grain, such as rice, corn (maize), wheat, oats, barley, or millet. In an embodiment, the bran is or includes wheat bran, oat bran or a mixture thereof. Subjects that are intolerant of wheat products can take a composition including only bran from grains other than wheat, e.g., oat bran. The bran can be in any of a variety of commercially available forms (e.g., flake or powder) for use in or for making the present composition.

Although not limiting to the present invention, it is believed that one cup of wheat bran contains 99% of the U.S. recommended daily allowance (RDA) of fiber, nine grams of protein, and 34% of the RDA for iron. Wheat bran is also high in protein, magnesium, manganese, niacin, phosphorus, zinc and vitamin B6, and is low in fat, with no cholesterol, and no sugar or sodium. Although not limiting to the present invention, it is believed that a powdered bran is about 25% more concentrated than a corresponding flake form of bran.

Any of a variety of commercially available cinnamon can be employed in the present composition. Although not limiting to the present invention, in certain embodiments, it is believed that one teaspoon of cinnamon contains 1 mg of iron, 1 mg of fiber, 28 mg of calcium, vitamin C, manganese, vitamin K, or a mixture thereof. The cinnamon can be in any of a variety of commercially available forms (e.g., ground or powder) for use in or for making the present composition.

Any of a variety of commercially available wheat germ oil that contains significant levels of octacosanol can be employed in the present composition. Suitable wheat germ oil is or includes unrefined and/or cold processed wheat germ oil. Suitable wheat germ oil can include over 1,000 mcg of octacosanol per tablespoon and can be a good source of vitamin E. The wheat germ oil can be in any of a variety of commercially available forms for use in or for making the present composition.

Any of a variety of commercially available gelatin suitable for consumption by mammals (e.g., humans or canines) can be employed in the present composition. The gelatin can be of animal (e.g., porcine) origin. The gelatin can be food-grade and edible. Suitable gelatin includes lysine, glycine, other amino acids, fatty acids, magnesium, calcium, or a mixture thereof. Although not limiting to the present invention, gelatin can be a protein food including 18 amino acids, but not being a complete source of amino acids. In an embodiment, tryptophan and cysteine are absent, and methionine is present at a relatively low level. Although not limiting to the present invention, gelatin can be a good source of the essential amino acid lysine, which occurs in relatively low proportions in, for example, cereal products. The gelatin can be in any of a variety of commercially available forms (e.g., powder or the shell of a capsule) for use in or for making the present composition.

Any of a variety of commercially available octacosanol can be employed in the present invention. The octacosanol can contain one or more long chain alcohols, such as triacontanol, tetracosanol, hexacosanol, or a mixture thereof. The octacosanol can be in any of a variety of commercially available forms (e.g., powder) for use in or for making the present composition. Amounts of octacosanol refer to the active ingredient, i.e., the octacosanol itself. In powder form a gram of the powder can contain, for example, 0.015 grams of octacosanol.

Any of a variety of flavoring, filler, excipient, or combination thereof can be employed in the present composition. Suitable flavors include stevia, cocoa, or a mixture thereof. Stevia is a sweetener that can be consumed by diabetics. Stevia may have other beneficial properties as well. The excipient can be or include a taste masking agent. The present composition can include a preservative, such as an antimicrobial agent and/or antioxidant, in an effective amount for extending the storage life of the composition.

For making a treat, a bar, or a wafer, the ingredients can be mixed with water and allowed to set to form a workable solid. Storage of the composition can be done at refrigerator temperatures, e.g., about 4° C. After the composition has set, it can be frozen.

As used herein, the phrase "consisting essentially of" refers to a composition including the listed ingredients and lacking any additional ingredients that would affect blood glucose levels. For example a composition consisting essentially of listed ingredients does not include sugar (e.g., sucrose, fructose, glucose, or the like). For example a composition of the present invention consisting essentially of listed ingredients does not include a medicine for treating diabetes.

Although not limiting to the present invention, in an embodiment, it is believed that administering an embodiment of the present composition can result in greater reduction in mammalian blood glucose levels than a composition lacking one or more of these ingredients. Although not limiting to the present invention, in an embodiment, it is believed that administering an embodiment of the present composition can result in greater reduction in mammalian blood glucose levels than would be expected based on activities of the ingredients separately. Although not limiting to the present invention, in an embodiment, it is believed that administering an embodiment of the present composition can result in greater reduction in mammalian blood glucose levels than would be expected based on components of the ingredients separately.

Insulin and Blood Glucose Levels

A diabetic subject taking the present composition may also be taking insulin, which also affects blood glucose levels. A blood glucose profile (or curve) is a graph of blood glucose levels over time. It is an effective way to determine the type, dose, and frequency of administration of insulin or other medication, necessary to keep the blood glucose at acceptable levels. Each subject (e.g., dog) can respond differently to insulin. Thus, the appropriate insulin therapy can be determined for each individual. In addition, a subject's (e.g., a dog's) insulin needs may change over time, so blood glucose profiles may performed periodically for the subject's lifetime.

By performing a blood glucose profile, a medical professional can determine if an insulin was effective, when the peak effect occurred (i.e., when the glucose level was at its nadir (lowest point)), how long the effect lasted, and the degree of fluctuation in the glucose level. Changes can then be made in the type of insulin or other medication, the dosage or the dosing intervals in order to maintain the blood glucose at the optimal level throughout a 24-hour period. In some cases, up to five or more blood glucose curves may need to be performed before a satisfactory regimen is determined. In addition to the blood glucose profile, the response of the subject is noted. For example, for a dog, the amount the dog is eating, drinking, and urinating; activity level; and weight all help determine if the insulin regimen is effective.

Other medicines employed to treat diabetes include biguanides (e.g., metformin), sulfonylureas (e.g., tolbutamide, glyburide, glipizide and others), α-glucosidase inhibitors (e.g., acarbose and miglitol) and thiazolidinediones (e.g., troglitazone and rosiglitazone). A subject receiving the present composition may be taking one or more of these medicines.

With the FPG test, a fasting blood glucose level between 100 and 125 mg/dl signals pre-diabetes. A person with a fasting blood glucose level of 126 mg/dl or higher has diabetes. In the OGTT test, a person's blood glucose level is measured after a fast and two hours after drinking a glucose-rich beverage. If the two-hour blood glucose level is between 140 and 199 mg/dl, the person tested has pre-diabetes. If the two-hour blood glucose level is at 200 mg/dl or higher, the person tested has diabetes.

Embodiments of Methods

In addition, in an embodiment, it has been observed that administering the present composition to healthy dogs improved the condition of their skin and/or coat and resulted in better overall general health (healthy weight and added lean muscle mass). In an embodiment, it has been observed that administering the present composition to dogs can improve skin condition, alleviate skin irritations, and facilitate general joint health. In an embodiment, it has been observed that administering the present composition can suppress appetite, influence weight loss, and/or increase muscle mass.

In an embodiment, the present invention includes a method of assisting weight loss in a human in need thereof. This embodiment includes administering the present composition. In an embodiment, the method includes administering to the dog a composition comprising: about 10 to about 45 wt-% yeast; about 10 to about 70 wt-% bran; about 2 to about 30 wt-% cinnamon; and about 5 to about 15 wt-% gelatin.

In an embodiment, the present invention includes a method of improving the quality of skin, hair, and/or nails in a human in need or desirous thereof. This embodiment includes administering the present composition. In an embodiment, the method includes administering to the dog a composition comprising: about 10 to about 45 wt-% yeast; about 10 to about 70 wt-% bran; about 2 to about 30 wt-% cinnamon; and about 5 to about 15 wt-% gelatin.

The present invention may be better understood with reference to the following examples. These examples are intended to be representative of specific embodiments of the invention, and are not intended as limiting the scope of the invention.

EXAMPLES

Example 1

A Composition of the Present Invention

Decreased and Steadied Blood Glucose Levels in Diabetic Does

An embodiment of the present composition, when administered twice daily to dogs also receiving insulin, resulted in decreased and steadied (more constant) blood glucose levels.

Materials and Methods

| Composition DT | |
| --- | --- |
| wt-% | Ingredient |
| 14 | brewer's yeast |
| 14 | wheat bran |
| 14 | oat bran |
| 7 | cinnamon |
| 7 | wheat germ oil |
| 7 | gelatin |
| 37 | water |

A single dose (treat) of composition DT is 0.75 ounces, which is 21 grams. Each canine was given a dose of composition DT, depending on their weight, in the form of a treat. Large dogs were given 3 treats, medium dogs 2 treats, and small dogs 1 treat per dose. Each canine received its dose after each insulin injection and followed by food twice per day. All dogs were receiving insulin at 12-hour intervals. Blood glucose levels were checked 6-7 hours post-injection.

| Name | Breed | Veterinarian | Insulin | Units of Insulin | DT Dose (twice per day) | FIG. |
| --- | --- | --- | --- | --- | --- | --- |
| Vincent | Italian Greyhound | A | Vetsulin | 24-28 decreased to 20 | 2 | 1 |
| Jackson | Mixed | A | Vetsulin | 20 | 1 | 2 and 3 |
| Peanut | Mixed | A | Vetsulin | 20 decreased to 18 | 1 | 4 and 5 |
| Indiana | Schnauzer | B | Vetsulin then Humulin | 20 decreased to 17 | 2 | 6 and 7 |
| Toto | Cairn Terrier | A | Vetsulin | 6 decreased to 5 | ½ | 8 and 9 |
| Babe | Yellow lab mix | C | Vetsulin then Humulin | 38 decreased to 25 | 3 | 10 and 11 |
| LuLu | Welsh Corgi Pen/Border Collie | A | Vetsulin then Humulin | decreased | 2 | 12 and 13 |
| Piper | Min Pin | E | Humulin | 16 decreased to 8 | 1 | 14 |
| Bailey | Brittany Spaniel Mix | A | Vetsulin then Humulin | to be determined | 2 | 15 |
| Rusty | Lassa Apsu | A | Humulin | to be determined | 2 | 16 |
| Maddie | Golden Retriever | D | Vetsulin | 36 decreased to 32 | 3 | |

Results

Before receiving composition DT, glucose levels for all canines were consistently high and uncontrolled for a substantial period of time. The dogs were typically taking maximum tolerated insulin doses. They could not maintain a consistent or normal blood glucose level while using insulin alone. Owners complained of their canine's excessive thirst and frequent nightly urination problems. All dogs were monitored by their veterinarian. Each of the plotted readings were taken 6-7 hours post injection, which should be in the middle of the nadir curve, for consistency and accuracy.

The combination of ingredients in composition DT produced positive results that are noticed quickly, usually within a few days. During treatment with composition DT, without exception, all the dogs' blood sugar levels were in the 75-140 normal range. The time to positive results seemed to be slightly longer for dogs receiving human insulin (e.g., HUMULIN N®) than VETSULIN®; 5 to 10 days compared to 2 to 5 days. Normal water consumption and lack of overnight urination resulted.

To demonstrate that composition DT was responsible for the decrease and steadying of blood glucose levels, six of the dogs then received no composition DT for one to two weeks. The following week's blood glucose levels were dramatically higher (242-586, FIGS. 3, 5, 9, 11, and 13). There was also a noticeable increase in water consumption and resultant frequent urination. Upon reinstating composition DT, urination, water consumption and blood glucose quickly returned to normal.

In addition, composition DT allows for a decreased dose of insulin for many of the canines in the study. Insulin dosages in many of the test subjects were dropped between 15-40%.

In two specific cases, diabetic dogs were given insulin shots and glucoses tested at 6 hours-post injection. These glucose levels were 260, and 242 respectively. After approximately 2 months of treatment with composition DT, the glucoses of these dogs were tested again 6 hours post insulin injection and were significantly reduced to 73, and 97.

Each of the dogs with results shown in the graphs has continued to take composition DT up to the filing date of this application, which includes periods from 6 to 18 months.

Additional benefits observed for the canines included: improved coat and/or skin; decreased or eliminated urinary tract infections; decreased or eliminated cataract formation and eventual blindness; normal water consumption and less frequent urination; normal appetite; healthy weight gain; more alert, playful and they appear to feel better.

At one point during the testing, VETSULIN® was taken off the market by the FDA. HUMULIN—N®, which is an insulin designed for humans, was substituted. This required adjustment of the insulin dosage. Composition DT was effective with either insulin.

Observations on Individual Canines:

Vincent is a member of the inventors' household. He had been an active and larger than usual Italian Greyhound weighing 22 pounds. As he developed diabetes, some 14 months before receiving composition DT, Vincent began drinking 1-2 gallons of water each day and losing weight rapidly. Vincent was started on VETSULIN® at this time. By two months before receiving composition DT, Vincent was nearly blind and weighed only 14 pounds. Blood glucose levels ranged from 275 to 392 (months −14 to −2)

After two weeks receiving composition DT, his weight was up to 20 pounds and he looked well. He returned to a normal level of water consumption, normal urination and overall healthy outlook. These improvements have been maintained for more than 18 months.

In week 3, Jackson did not receive DT for four days prior to blood glucose test, and level increased to 238.

Before entering the study, Peanut had been treated with insulin without attaining stable blood glucose levels. In week 3, Peanut did not receive DT for four days prior to blood glucose test, and level increased to near 300.

Indiana lost half of his body weight before starting composition DT. LuLu was due to be euthanized before starting on composition DT, but the improvement due this composition has provided LuLu with a good quality of life.

Maddie was also due to be euthanized before starting on composition DT, but she made a full recovery. While taking twice daily doses of composition DT, Maddie was reported to be seizure free, to have brighter eyes, to be very alert, to exhibit improved appetite with healthy weight gain. She went to the bathroom and walked outside by herself, is drinking only normal amounts or water and has had no accidents.

Conclusions

An embodiment of the present composition, when administered twice daily to dogs also receiving insulin, resulted in decreased and steadied (more constant) blood glucose levels. Essentially, the composition DT seemed to smooth out glucose levels.

Example 2

A Composition of the Present Invention

Lowered Human Blood Glucose Levels

An embodiment of the present composition lowered human blood glucose levels.

Materials and Methods

| Composition HB | |
| --- | --- |
| wt-% | Ingredient |
| 12 | brewer's yeast |
| 12 | wheat bran |
| 12 | oat bran |
| 6 | cinnamon |
| 6 | wheat germ oil |
| 6 | gelatin |
| 7 | flavor (optional) |
| 1 | octacosanol (optional) |
| 38 | water |

A unit dose of composition HB is a 0.85 ounce (24 gram) portion (bar) of this mixture.

The subject of the study was a 47 year old male Caucasian non-diabetic, height 6'1", and weight 225 pounds at the beginning of the study. Subject is a non-smoker and does a moderate level of exercise—walking 3-4 miles/2(×) week.

This study included monitoring food intake and blood glucose levels at various critical times of the day. Subject tested blood glucose level at the ½ hour range after a meal (maximum spike), 1 hour and 1.5 hour ranges and after 2 hours (normal recovery time for non-diabetic). Subject purchased a blood glucose monitor, followed all instructions and tested for accuracy with its built in monitors.

Subject tracked all food and beverage intake and consumed 1 alcohol drink (beer or wine) 5-6 nights per week with dinner. The subject consumed the same meals before and after the intake of composition HB for comparison and accuracy. Exercise was monitored and consistent during testing. Subject was taking vitamins and supplements prior to the study, but stopped taking any 10 days prior to the beginning of the study period.

The initial study was conducted for 23 days (part I) and continued thereafter (part II on-going testing). The time period without the use of composition HB was 13 days of part I. The time period with the use of composition HB was the other 10 days of part I. During this phase the dose was equal to one dose of composition HB, repeated three times per day, one before each meal. Composition HB was taken with 8-12 ounces of water prior to each meal.

The subject ate the same breakfasts with and without consuming composition HB. Breakfast #1—High 5 Breakfast: 2 eggs, 2 bacon, 2 sausage, 1—12" pancake with maple syrup, large portion hash browns, ketchup and 12 oz of Skim Milk and water. Breakfast #2—High Sugar/Carb: Bowl of shredded wheat squares, 8 oz skim milk, one medium organic orange and 10 oz of fresh pineapple.

Results

Figure 17:
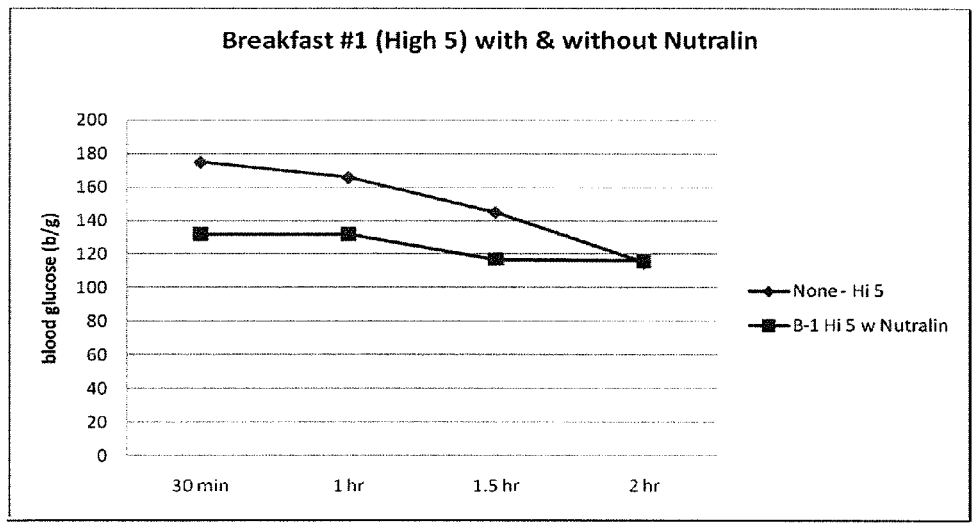
FIG. 17 is a graph that illustrates that a human subject's after-breakfast blood glucose levels decreased upon treatment with a composition of the present invention (referred to in the Figure as Nutralin).

Breakfast #1—FIG. 17

This breakfast was high in calorie, fat, sugar and carbohydrates. Blood glucose tended to be kept in a tighter range without dramatic ranges (peaks and troughs). Although the subject felt full longer and had no need to eat lunch, the subject felt good. Composition HB in the first hour consistently reduced the upper blood glucose level by 30+ points (170 vs 140 at ½ hour and at one hour 166 vs 130 and 1.5 hours 145 vs. 120). A subject should be back normal range of 120 or less no matter what they eat, assuming that they do not have diabetes or another problem with control of blood glucose levels.

Figure 18:
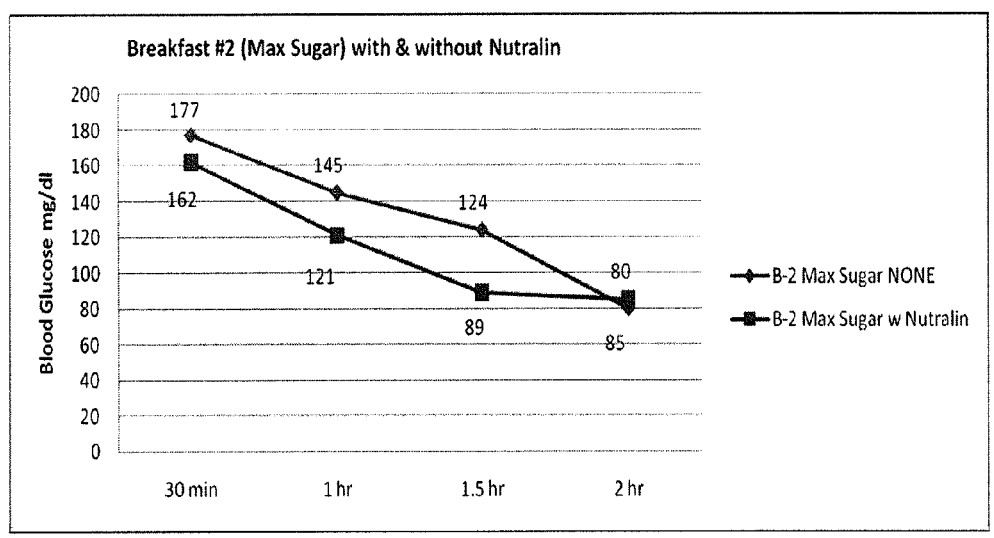
FIG. 18 is a graph that illustrates that a human subject's after-sugary-breakfast blood glucose levels decreased at a comfortable rate upon treatment with a composition of the present invention (referred to in the Figure as Nutralin).

Breakfast #2(Max Sugar)—FIG. 18

This breakfast was very high in sugar and carbohydrates. The subject did not feel good after eating this breakfast. The subject's blood glucose reading spiked at the ½ hour level and dropped very rapidly in one hour. Blood glucose dropped approximately 100 points in the absence of dosing with composition HB. In the first ½ hour the difference was 177 (none) vs. a range of 160. At the one hour time frame, it was 145 vs. 120 and at the 1½ hour span it was 124 vs 88 and at two hours all were in the 80 range. This breakfast resulted in high highs and low lows all in a short time span and the subject felt the difference. With composition HB the range was 160 to 88 (total drop 72) and without 177 to 80 (total drop 97 points).

Discussion

Using composition HB, the subject experienced more consistent blood glucose levels with no noticeable spikes. Due to more consistent blood glucose levels subject did not experience the afternoon drowsiness from eating lunch after taking composition HB, which he had experienced for years when not taking composition HB. Subject noticed consistent energy level throughout the day. After long day of reading, the subject did not experience the 5:30 p.m. blurred vision due to the drop in blood sugar levels prior to dinner. General eye strain from working on a computer was alleviated. Subject also observed that cravings for sugar were curbed.

Upon a medical examination by a doctor who also reviewed the data reported here, the doctor concluded that the subject would be likely to develop Type II Diabetes if left unchecked. Also, the upper ranges after eating breakfast also indicated pre-diabetes.

Subject's spouse has no blood glucose issues and observed that composition HB acted as a multi-vitamin, but had little or no effect on her blood glucose readings. However, it was observed that effects of taking composition HB included noticeable weight loss, skin, hair, nail improvement, and reduced cholesterol. Taking composition HB, the spouse lost 8 pounds that she had been unable to lose even when she had been following a very strict diet without taking composition HB.

Example 3

A Form of a Composition of the Present Invention in a Gelatin Capsule

A capsule form of the present composition included:

| Composition HC | |
|---|---|
| wt-% | Ingredient |
| 33 | brewer's yeast |
| 19 | wheat bran (powder) |
| 19 | oat bran (powder) |
| 19 | cinnamon |
| 9 | gelatin |
| 1.6 | chromium enriched yeast (optional) |

Composition HC was in a gelatin capsule. Composition HC can be administered with a 1 g dose of wheat germ oil. The wheat germ oil can also be in a gelatin capsule. In an embodiment, the present composition includes one or more capsules of composition HC and wheat germ oil, e.g., capsules containing wheat germ oil.

Composition HC can be administered to an adult human in doses of 0.22 oz (6.4 g), the dose being repeated 3 times per day. In an embodiment, composition HC can be administered in capsules containing 0.032 oz (0.9 g) each, which amounts to 7 capsules per dose.

Example 4

A Composition of the Present Invention

Showed No Side-Effects in Healthy Humans

An embodiment of the present composition was evaluated in a Phase I clinical trial for its safety and effect on blood glucose levels in healthy humans.

Protocol

This study evaluated the change in glucose levels and insulin levels in normal healthy subjects after taking composition HB initially and after one week. The dosage was two 0.85 ounce bars of composition HB taken three times per day. The study was conducted according to all relevant safeguards, institutional requirements, and regulatory agency requirements.

The study included measuring changes in glucose over time; evaluating the peak and trough action of composition HB or HC on glucose at baseline; evaluating the peak and trough action of composition HB or HC on insulin levels at baseline; evaluating the peak and trough glucose levels after a week long loading dose; and/or evaluating the peak and trough insulin levels after a week long loading dose.

This exploratory pilot study was a non-blind, single-subject design that evaluated 10 non-diabetic subjects' insulin and glucose responses to composition HB. Subjects took part in the study for up to 14 days. There were two phases to the study. Phase I included screening and baseline assessments for self-comparison in the absence of treatment. Phase II included the same assessments in the presence of treatment with an exemplified embodiment of the claimed composition.

Exclusion criteria included, for example, in the opinion of the investigator the subject was not a good candidate for the study; the subject had current and active liver or kidney disease; lab abnormalities of greater than 3 times the upper limit of normal for any lab value; and/or diabetes.

The study procedures included one of more of the following:

|  | Screening | Glucose and insulin baseline | Treatment Baseline/ Treatment start | End of Treatment |
|---|---|---|---|---|
| VISIT | 1 | 2 | 3 | 4 |
| Day | −7 | 1 | 7 | 14 |
| PROCEDURE |  |  |  |  |
| Medical History | x | x |  |  |
| Physical Exam | x | x |  | x |
| CBC with differential | x |  |  |  |
| Comprehensive Metabolic Panel | x |  |  |  |
| Hemaglobin A1C |  | x |  |  |
| Glucose tolerance test |  | x |  |  |
| Glucose tolerance test with composition HB or HC |  |  | x | x |
| Insulin levels |  | x | x | x |
| Vital Signs (weight, blood pressure, pulse, temperature) |  | x | x | x |
| Concomitant Medication Adverse Event Review | x | x | x | x |
| A symptoms diary will be dispensed/collected |  |  | x | x |
| Dispense composition HB or HC |  |  | x |  |
| Record Adverse Effects |  | x | x | x |
| Administer Questionnaires |  |  |  | x |

Results

A preliminary phase I clinical study administering composition HB was conducted with healthy individuals to establish safety and to determine side effects. Eleven subjects were recruited for the study. One subject signed consent and then withdrew after one visit. Five subjects started the study and withdrew consent after one week on study. The study ended with five subjects completing three weeks of taking 2 doses of composition HB three times per day.

The results showed minimal side effects. Five subjects reported nausea and vomiting. Subjects monitored their glucose levels at home and experienced no episodes of hypoglycemia. Composition HB was safe and had a slight effect on blood glucose and insulin levels in normal individuals. Most subjects rated the taste, texture, and appearance of the product as unsatisfactory.

Discussion

Based on this phase I study, the institution that conducted the phase I study decided to conduct a double blind clinical trial involving 40 type II diabetics. Then medical professionals planning the study expect that the composition of the present invention will have a greater effect on type II diabetic individuals as they have less control of their blood sugar than, for example, pre-diabetic individuals. The clinical trial is being conducted to demonstrate whether or not, by taking composition HC or composition HB, diabetics will be able to maintain a (more) stable blood glucose level and benefit from increased sensitivity to insulin. The research is also expected to show that diabetic individuals may be able to reduce their level of insulin and/or other medications while taking composition HC or composition HB.

Example 5

A Composition of the Present Invention is Studied for

Safety and Efficacy in Type-II Diabetic Humans

This study will be a phase II, placebo controlled, randomized, safety and efficacy study to evaluate the change in hemoglobin A1C levels in type 2 diabetic subjects while taking composition HC.

Hypothesis

The hypothesis of this study is that diabetic subjects will decrease hemoglobin A1C levels by ≥2.0 after taking composition HC for 26 weeks. This is a phase II safety and efficacy study to evaluate the change in hemoglobin A1C, glucose levels, and medication usage in diabetic subjects while taking composition HC. Clinical outcomes are expected to include: hemoglobin A1C reduction; a reduction in blood glucose levels; reducing the amount of diabetes medication needed.

Protocol

Subjects will take part in the study for up to 26 weeks. All subjects will be given placebo capsules for the first week, to measure compliance prior to randomization. The subjects will be type II Diabetics who have been stable on diabetes medication/Insulin for 3 months or greater.

Blood will be drawn for laboratory tests such as: comprehensive metabolic panel, complete blood count, hemoglobin A1C, chromium levels, insulin level, C-peptide levels (to verify the subject is a type II diabetic), fasting insulin levels, genetic analysis (endocrine expression genetics), and the like.

Example 6

A Composition of the Present Invention Reduced Seizures in Does

An embodiment of the present composition, when administered twice daily to dogs that suffer from seizures, reduced the number of seizures.

Materials and Methods

Each canine was given a dose of composition DT, depending on their weight, in the form of a treat. Large dogs were given 3 treats, medium dogs 2 treats, and small dogs 1 treat per dose. Each canine received its dose followed by food twice per day.

Results

Leo, the 6-year old brother of Vincent, formerly suffered from about 2 seizures per year, typically when over excited. In the 15 months of receiving twice daily doses of composition DT, Leo has suffered no seizures. His coat and skin have also improved.

Charlie is a beagle who suffered from regular seizures. He was on composition DT without seizures for a period of about one month. Composition DT was removed for ten days, during which time Charlie had a seizure. After resuming treatment with composition DT, Charlie has gone several months without a seizure.

Maddie had been having 2 or 3 seizures per day before starting composition DT. She has had no seizures while receiving her twice daily dosage of composition DT.

Conclusions

An embodiment of the present composition, when administered twice daily to dogs that suffer from seizures, reduced the number of seizures.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

We claim:

1. A method of reducing a blood glucose level in a canine subject in need thereof, the method comprising administering to the subject a composition comprising:
    about 10 to about 45 wt-% yeast;
    about 10 to about 70 wt-% bran;
    about 2 to about 30 wt-% cinnamon; and
    about 5 to about 15 wt-% gelatin;
wherein administering is effective to lower the required dose of insulin for effective glucose control and to stabilize blood glucose levels.

2. The method of claim 1, wherein the subject also receives insulin to control the blood glucose level.

3. The method of claim 2, comprising administering the composition within one hour after the subject receives a dose of insulin.

4. The method of claim 1, comprising administering the composition within one hour before a meal.

5. The method of claim 1, wherein the composition further comprises an ingredient selected from the group consisting of:
    about 5 to about 15 wt-% wheat germ oil;
    about 5 to about 30 wt-% flavoring;
    about 0.1 to about 2 wt-% octacosanol;
    about 0.5 to about 3 wt-% chromium enhanced yeast; and
    a mixture thereof.

6. The method of claim 1, wherein:
    the bran comprises approximately equal amounts of wheat bran and oat bran.

7. The method of claim 1, wherein the composition comprises:
    about 22 wt-% brewers yeast;
    about 44 wt-% bran;
    about 11 wt-% cinnamon;
    about 11 wt-% gelatin; and
further comprises about 11 wt-% wheat germ oil.

8. The method of claim 1, wherein the composition comprises:
    about 17 wt-% brewers yeast;
    about 34 wt-% bran;
    about 9 wt-% cinnamon;
    about 9 wt-% gelatin; and
further comprises:
    about 9 wt-% wheat germ oil;
    about 17 wt-% flavoring; and
    about 0.7 wt-% octacosanol.

9. The method of claim 1, wherein the composition comprises:
    about 33 wt-% brewers yeast;
    about 38 wt-% bran;
    about 19 wt-% cinnamon;
    about 9 wt-% gelatin; and
further comprises about 1.6 wt-% chromium enhanced yeast.

10. A method of reducing a blood glucose level in a canine subject in need thereof, the method comprising administering to the subject a composition comprising:
    about 17 wt-% brewers yeast;
    about 34 wt-% bran;
    about 9 wt-% cinnamon;
    about 9 wt-% gelatin;
    about 9 wt-% wheat germ oil;
    about 17 wt-% flavoring; and
    about 0.7 wt-% octacosanol;
wherein administering is effective to lower the required dose of insulin for effective glucose control and to stabilize blood glucose levels.

11. A method of reducing a blood glucose level in a canine subject in need thereof, the method comprising administering to the subject a composition comprising:
    about 33 wt-% brewers yeast;
    about 38 wt-% bran;
    about 19 wt-% cinnamon;
    about 9 wt-% gelatin; and
    about 1.6 wt-% chromium enhanced yeast;
wherein administering is effective to lower the required dose of insulin for effective glucose control and to stabilize blood glucose levels.

12. The method of claim 1, wherein the yeast is selected from the group consisting of brewers yeast, chromium enhanced yeast, and a mixture thereof.

13. The method of claim 1, wherein:
    the bran comprises approximately equal amounts of wheat bran and oat bran; and
    the yeast is selected from the group consisting of brewers yeast, chromium enhanced yeast, and a mixture thereof.

* * * * *